(12) United States Patent
Krueger

(10) Patent No.: US 6,193,648 B1
(45) Date of Patent: Feb. 27, 2001

(54) CARDIAC CONSTRAINT WITH DRAW STRING TENSIONING

(75) Inventor: Kurt D. Krueger, Stacy, MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 0 days.

(21) Appl. No.: 09/400,019

(22) Filed: Sep. 21, 1999

(51) Int. Cl.$^7$ ...................................... A61F 13/00

(52) U.S. Cl. ................................. 600/37; 623/3

(58) Field of Search ................ 600/37, 16–18; 623/3; 607/129

(56) References Cited

U.S. PATENT DOCUMENTS

| | | |
|---|---|---|
| 3,983,863 | 10/1976 | Janke et al. . |
| 4,048,990 | 9/1977 | Goetz . |
| 4,403,604 | 9/1983 | Wilkinson et al. . |

(List continued on next page.)

FOREIGN PATENT DOCUMENTS

| | | |
|---|---|---|
| 3831540 | 4/1989 | (DE) . |
| 3831540 | 6/1993 | (DE) . |
| 295 17 393 U1 | 3/1996 | (DE) . |
| 0 280 564 | 8/1988 | (EP) . |
| 2209678 | 5/1989 | (GB) . |
| 60-203250 | 10/1985 | (JP) . |
| 1-145066 | 6/1989 | (JP) . |
| 1009457 | 4/1983 | (SU) . |
| WO 98/29041 | 7/1998 | (WO) . |
| WO 98/58598 | 12/1998 | (WO) . |
| WO 99/44534 | 9/1999 | (WO) . |

OTHER PUBLICATIONS

"Abstracts From the 68th Scientific Sessions, Anaheim Convention Center, Anaheim, California, Nov. 13–16, 1995", *American Heart Association Supplement to Circulation*, vol. 92, No. 8, Abstracts 1810–1813 (Oct. 15, 1995).

Capomolla et al., "Dobutamine and nitroprusside infusion in patients with severe congestive heart failure: Hemodynamic improvement by discordant effects on mitral regurgitation, left atrial function, and ventricular function", *American Heart Journal*, vol. 134, No. 6, pp. 1089–1098 (Dec. 1997).

Capouya et al., "Girdling Effect of Nonstimulated Cardiomyoplasty on Left Ventricular Function", *The Society of Thoracic Surgeons*, vol. 56, pp. 867–871 (1993).

(List continued on next page.)

Primary Examiner—John P. Lacyk
(74) Attorney, Agent, or Firm—Merchant & Gould P.C.

(57) ABSTRACT

A method and apparatus for treating congestive heart disease and related cardiac complications such as valvular disorders includes a constraining device placed on the heart. The constraining device is a jacket of flexible material of knit construction defining a volume between an open upper end and a lower end. The jacket is dimensioned for the apex of the heart to be inserted into the volume through the open upper end and for the jacket to be slipped over the heart. The jacket is further dimensioned for the jacket to have a longitudinal dimension between the upper and lower ends sufficient for said jacket to constrain said lower portion of the heart. The jacket adapted to be adjusted on the heart to snugly conforming to an external geometry of the heart to constrain circumferential expansion of the heart beyond. A flexible drawstring is laced through the jacket material for the knit material to be bunched together as one end of the drawstring is pulled. A releasable stay member is provided for holding the draw string in a fixed position relative to said jacket upon release of a pulling tension on the draw string with the stay member releasable in response to a resumed pulling tension on the draw string.

2 Claims, 7 Drawing Sheets

U.S. PATENT DOCUMENTS

| | | |
|---|---|---|
| 4,428,375 | 1/1984 | Ellman . |
| 4,630,597 | 12/1986 | Kantrowitz et al. . |
| 4,690,134 | 9/1987 | Snyders . |
| 4,821,723 | 4/1989 | Baker, Jr. et al. . |
| 4,834,707 | 5/1989 | Evans . |
| 4,878,890 | 11/1989 | Bilweis . |
| 4,936,857 | 6/1990 | Kulik . |
| 4,957,477 | 9/1990 | Lundback . |
| 4,973,300 | 11/1990 | Wright . |
| 4,976,730 | 12/1990 | Kwan-Gett . |
| 5,057,117 | 10/1991 | Atweh . |
| 5,087,243 | 2/1992 | Avitall . |
| 5,131,905 | 7/1992 | Grooters . |
| 5,150,706 | 9/1992 | Cox et al. . |
| 5,186,711 | 2/1993 | Epstein . |
| 5,192,314 | 3/1993 | Daskalakis . |
| 5,256,132 | 10/1993 | Snyders . |
| 5,290,217 | 3/1994 | Campos . |
| 5,356,432 | 10/1994 | Rutkow et al. . |
| 5,383,840 | 1/1995 | Heilman et al. . |
| 5,385,156 | 1/1995 | Oliva . |
| 5,429,584 | 7/1995 | Chiu . |
| 5,507,779 | 4/1996 | Altman . |
| 5,524,633 | 6/1996 | Heaven et al. . |
| 5,603,337 | 2/1997 | Jarvik . |
| 5,647,380 | 7/1997 | Campbell et al. . |
| 5,702,343 | 12/1997 | Alferness . |
| 5,713,954 | 2/1998 | Rosenberg et al. . |
| 5,800,528 | 9/1998 | Lederman et al. . |

OTHER PUBLICATIONS

Cohn, "The Management of Chronic Heart Failure", *The New England Journal of Medicine*, vol. 335, No. 7, pp. 490–498 (Aug. 15, 1996).

Coletta et al., "Prognostic value of left ventricular volume response during dobutamine stress echocardiograpy", *European Heart Journal*, vol. 18, pp. 1599–1605 (Oct. 1997).

Guasp, "Una protesis contentiva para el tratamiento de la miocardiopatia dilatada", *Revista Espanola de Cardiologia*, vol. 51, No. 7, pp. 521–528 (Jul. 1998).

Kass et al., "Reverse Remodeling From Cardiomyoplasty in Human Heart Failure", *Circulation*, vol. 91, No. 9, pp. 2314–2318 (May 1, 1995).

Levin et al., "Reversal of Chronic Ventricular Dilation in Patients With End–Stage Cardiomyopathy by Prolonged Mechanical Unloading", *Circulation*, vol. 91, No. 11, pp. 2717–2720 (Jun. 1, 1995).

Oh et al., "The Effects Of Prosthetic Cardiac Binding And Adynamic Cardiomyoplasty In A Model Of Dilated Cardiomyopathy", *The Journal of Thoracic and Cardiovascular Surgery*, vol. 116, No. 1, pp. 148–153 (Jul. 1998).

Paling, "Two–Bar Fabrics (Part–Set Threading)", *Warp Knitting Technology*, Columbine Press (Publishers) Ltd., Buxton, Great Britain, p. 111 (1970).

Vaynblat et al., "Cardiac Binding in Experimental Heart Failure", *Ann Thorac Surg*, vol. 64 (1997).

CARDIAC CONSTRAINT WITH DRAW STRING TENSIONING

I. BACKGROUND OF THE INVENTION

1. Field of the Invention

The present invention pertains to a method and apparatus for treating congestive heart disease and related valvular dysfunction. More particularly, the present invention is directed to a cardiac constraint having a releasable tensioning member to tension the constraint on a heart.

2. Description of the Prior Art

Congestive heart disease is a progressive and debilitating illness. The disease is characterized by a progressive enlargement of the heart.

As the heart enlarges, the heart is performing an increasing amount of work in order to pump blood each heart beat. In time, the heart becomes so enlarged the heart cannot adequately supply blood. An afflicted patient is fatigued, unable to perform even simple exerting tasks and experiences pain and discomfort. Further, as the heart enlarges, the internal heart valves may not adequately close. This impairs the function of the valves and further reduces the heart's ability to supply blood.

Causes of congestive heart disease are not fully known. In certain instances, congestive heart disease may result from viral infections. In such cases, the heart may enlarge to such an extent that the adverse consequences of heart enlargement continue after the viral infection has passed and the disease continues its progressively debilitating course.

Patients suffering from congestive heart disease are commonly grouped into four classes (i.e., Classes I, II, III and IV). In the early stages (e.g., Classes I and II), drug therapy is the most commonly prescribed treatment. Drug therapy treats the symptoms of the disease and may slow the progression of the disease. Importantly, there is no cure for congestive heart disease. Even with drug therapy, the disease will progress. Further, the drugs may have adverse side effects.

Presently, the only permanent treatment for congestive heart disease is heart transplant. To qualify, a patient must be in the later stage of the disease (e.g., Classes III and IV with Class IV patients given priority for transplant). Such patients are extremely sick individuals. Class III patients have marked physical activity limitations and Class IV patients are symptomatic even at rest.

Due to the absence of effective intermediate treatment between drug therapy and heart transplant, Class III and IV patients will have suffered terribly before qualifying for heart transplant. Further, after such suffering, the available treatment is unsatisfactory. Heart transplant procedures are very risky, extremely invasive and expensive and only shortly extend a patient's life. For example, prior to transplant, a Class IV patient may have a life expectancy of 6 months to one-year. Heart transplant may improve the expectancy to about five years.

Unfortunately, not enough hearts are available for transplant to meet the needs of congestive heart disease patients. In the United States, in excess of 35,000 transplant candidates compete for only about 2,000 transplants per year. A transplant waiting list is about 8–12 months long on average and frequently a patient may have to wait about 1–2 years for a donor heart. While the availability of donor hearts has historically increased, the rate of increase is slowing dramatically. Even if the risks and expense of heart transplant could be tolerated, this treatment option is becoming increasingly unavailable Further, many patients do not qualify for heart transplant due to failure to meet any one of a number of qualifying criteria.

Congestive heart failure has an enormous societal impact. In the United States alone, about five million people suffer from the disease (Classes I through IV combined). Alarmingly, congestive heart failure is one of the most rapidly accelerating diseases (about 400,000 new patients in the United States each year). Economic costs of the disease have been estimated at $38 billion annually.

Not surprising, substantial effort has been made to find alternative treatments for congestive heart disease. Recently, a new surgical procedure has been developed. Referred to as the Batista procedure, the surgical technique includes dissecting and removing portions of the heart in order to reduce heart volume. This is a radical new and experimental procedure subject to substantial controversy. Furthermore, the procedure is highly invasive, risky and expensive and commonly includes other expensive procedures (such as a concurrent heart valve replacement). Also, the treatment is limited to Class IV patients and, accordingly, provides no hope to patients facing ineffective drug treatment prior to Class IV. Finally, if the procedure fails, emergency heart transplant is the only available option.

Clearly, there is a need for alternative treatments applicable to both early and later stages of the disease to either stop the progressive nature of the disease or more drastically slow the progressive nature of congestive heart disease. Unfortunately, currently developed options are experimental, costly and problematic.

Cardiomyoplasty is a recently developed treatment for earlier stage congestive heart disease (e.g., as early as Class III dilated cardiomyopathy). In this procedure, the latissimus dorsi muscle (taken from the patient's shoulder) is wrapped around the heart and chronically paced synchronously with ventricular systole. Pacing of the muscle results in muscle contraction to assist the contraction of the heart during systole.

Even though cardiomyoplasty has d monstrated symptomatic improvement, studies suggest the procedure only minimally improves cardiac performance. The procedure is highly invasive requiring harvesting a patient's muscle and an open chest approach (i.e., sternotomy) to access the heart. Furthermore, the procedure is expensive—especially those using a paced muscle. Such procedures require costly pacemakers. The cardiomyoplasty procedure is complicated. For example, it is difficult to adequately wrap the muscle around the heart with a satisfactory fit. Also, if adequate blood flow is not maintained to the wrapped muscle, the muscle may necrose. The muscle may stretch after wrapping reducing its constraining benefits and is generally not susceptible to post-operative adjustment. Finally, the muscle may fibrose and adhere to the heart causing undesirable constraint on the contraction of the heart during systole.

While cardiomyoplasty has resulted in symptomatic improvement, the nature of the improvement is not understood. For example, one study has suggested the benefits of cardiomyoplasty are derived less from active systolic assist than from remodeling, perhaps because of an external elastic constraint. The study suggests an elastic constraint (i.e., a non-stimulated muscle wrap or an artificial elastic sock placed around the heart) could provide similar benefits. Kass et al., *Reverse Remodeling, From Cardiomyoplasty In Human Heart Failure: External Constraint Versus Active Assist*, 91 *Circulation* 2314–2318 (1995). Similarly, cardiac binding is described in Oh et al., *The Effects of Prosthetic*

Cardiac Binding and A dynamic Cardiomyoplasty in a Model of Dilated Cardiomyopathy, 116 J. Thorac. Cardiovasc. Surg. 148–153 (1998), Vaynblat et al., Cardiac Binding in Experimental Heart Failure, 64 Ann. Thorac. Surg. 81–85 (1997) and Capouya et al., Girdling Effect of Nonstimulated Cardiomyoplasty on Left Ventricular Function, 56 Ann. Thorac. Surg. 867–871 (1993).

In addition to cardiomyoplasty, mechanical assist devices have been developed as intermediate procedures for treating congestive heart disease. Such devices include left ventricular assist devices ("LVAD") and total artificial hearts ("TAH"). An LVAD includes a mechanical pump for urging blood flow from the left ventricle into the aorta. Such surgeries are expensive. The devices are at risk of mechanical failure and frequently require external power supplies. TAH devices are used as temporary measures while a patient awaits a donor heart for transplant.

Commonly assigned U.S. Pat. No. 5,702,343 to Alferness dated Dec. 30, 1997 teaches a jacket to constrain cardiac expansion during diastole. Also, PCT International Publication No. WO 98/29401 published Jul. 9, 1998 teaches a cardiac constraint in the form of surfaces on opposite sides of the heart with the surfaces joined together by a cable through the heart or by an external constraint. U.S. Pat. No. 5,800,528 dated Sep. 1, 1998 teaches a passive girdle to surround a heart. German utility model DE 295 17 393 describes a non-expansible heart pouch. PCT International Publication No. WO 98/58598 published Dec. 30, 1998 describes a cardiac pouch with an elastic limit.

A cardiac constraint device can be placed on an enlarged heart and fitted snug during diastole. For example, a knit jacket device can be loosely slipped on the heart. After such placement, the material of the jacket can be gathered to adjust the device to a desired tension. The gathered material can be sutured or otherwise fixed to maintain the tensioning. The heart may be pre-shrunk prior to placement of the device or the device may be fitted on the heart without pre-shrinking the heart. The device is adjusted to a snug fit on the heart during diastole.

The present invention is directed to improved ways to facilitate the tensioning and gathering of material of the device on the heart.

II. SUMMARY OF THE INVENTION

According to a preferred embodiment of the present invention, a method and apparatus are disclosed for treating congestive heart disease and related cardiac complications such as valvular disorders. A constraining device is placed on the heart. The constraining device is a jacket of flexible material of knit construction defining a volume between an open upper end and a lower end. The jacket is dimensioned for the apex of the heart to be inserted into the volume through the open upper end and for the jacket to be slipped over the heart. The jacket is further dimensioned for the jacket to have a longitudinal dimension between the upper and lower ends sufficient for the jacket to constrain the lower portion of the heart. The jacket is adapted to be adjusted on the heart to snugly conform to an external geometry of the heart. A flexible drawstring is laced through the jacket material for the knit material to be bunched together as one end of the drawstring is pulled. A releasable stay member is provided for holding the draw string in a fixed position relative to the jacket upon release of a pulling tension on the draw string with the stay member releasable in response to a resumed pulling tension on the draw string.

IV. DESCRIPTION OF THE PREFERRED EMBODIMENT

A. Congestive Heart Disease

Figure 1A:
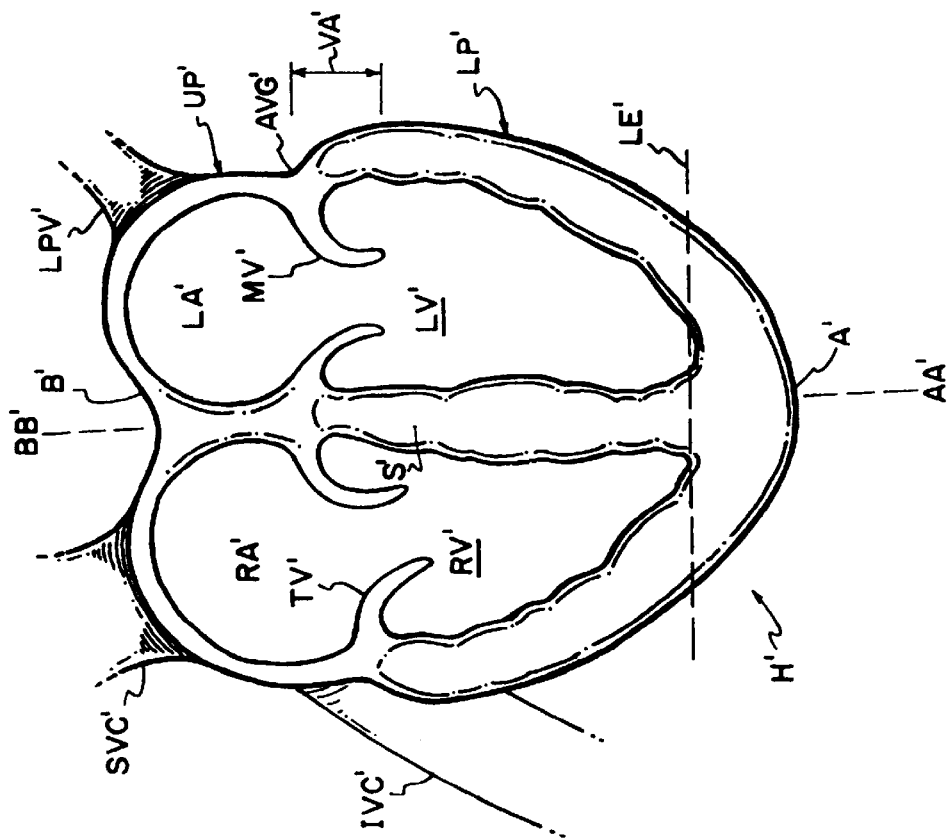
FIG. 1A is the view of FIG. 1 showing the heart during diastole.

To facilitate a better understanding of the present invention, description will first be made of a cardiac constraint device such as is more fully described in commonly assigned and copending U.S. patent application Ser. No. 09/114,757 filed Jul. 13, 1998. In the drawings, similar elements are labeled similarly throughout.

Figure 1:
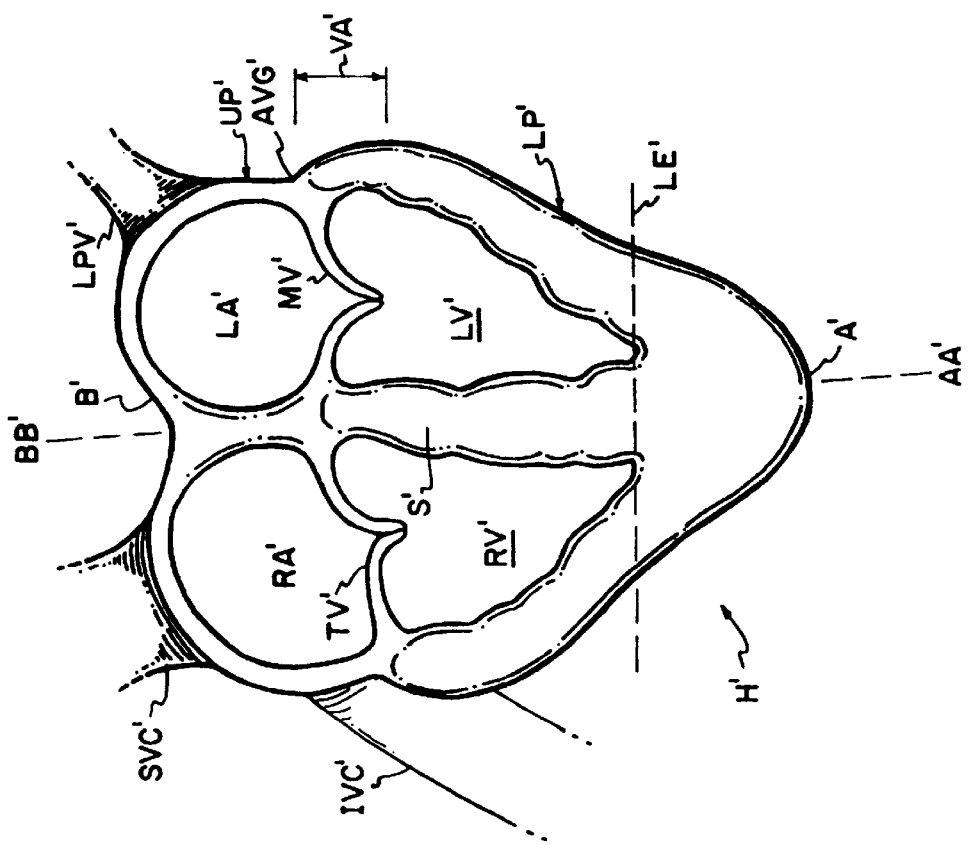
FIG. 1 is a schematic cross-sectional view of a normal, healthy human heart shown during systole.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum S'. The myocardium MYO' and septum S' define four internal heart chambers including a right atrium RA', a left atrium LA', a right ventricle RV' and a left ventricle LV'. The heart H' has a length measured along a longitudinal axis BB'–AA' from an upper end or base B' to a lower end or apex A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced therefrom by the thickness of the myocardium MYO'.

Due to the compound curves of the upper and lower portions UP', LP', the upper and lower portions UP', LP' meet at a circumferential groove commonly referred to as the A-V (atrio-ventricular) groove AVG'. Extending away from the upper portion UP' are plurality of major blood vessels communicating with the chambers RA', RV', LA', LV'. For ease of illustration, only the superior vena cava SVC', inferior vena cava IVC' and a left pulmonary vein LPV' are shown as being representative.

The heart H' contains valves to regulate blood flow between the chambers RA', RV', LA', LV' and between the chambers and the major vessels (e.g., the superior vena cava SVC', inferior vena cava IVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A-V groove AVG' and referred to as the valvular annulus VA'. The valves TV' and MV' open and close through the beating cycle of the heart H.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. IA), the heart H' is expanding and the conical shape of the lower portion LP' bulges radically outwardly (relative to axis AA'–BB').

The motion of the heart H' and the variation in the shape of the heart H' during contraction and expansion is complex. The amount of motion varies considerably throughout the heart H'. The motion includes a component which is parallel to the axis AA'–BB' (conveniently referred to as longitudinal expansion or contraction). The motion also includes a component perpendicular to the axis AA'–BB' (conveniently referred to as circumferential expansion or contraction).

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Figure 2A:
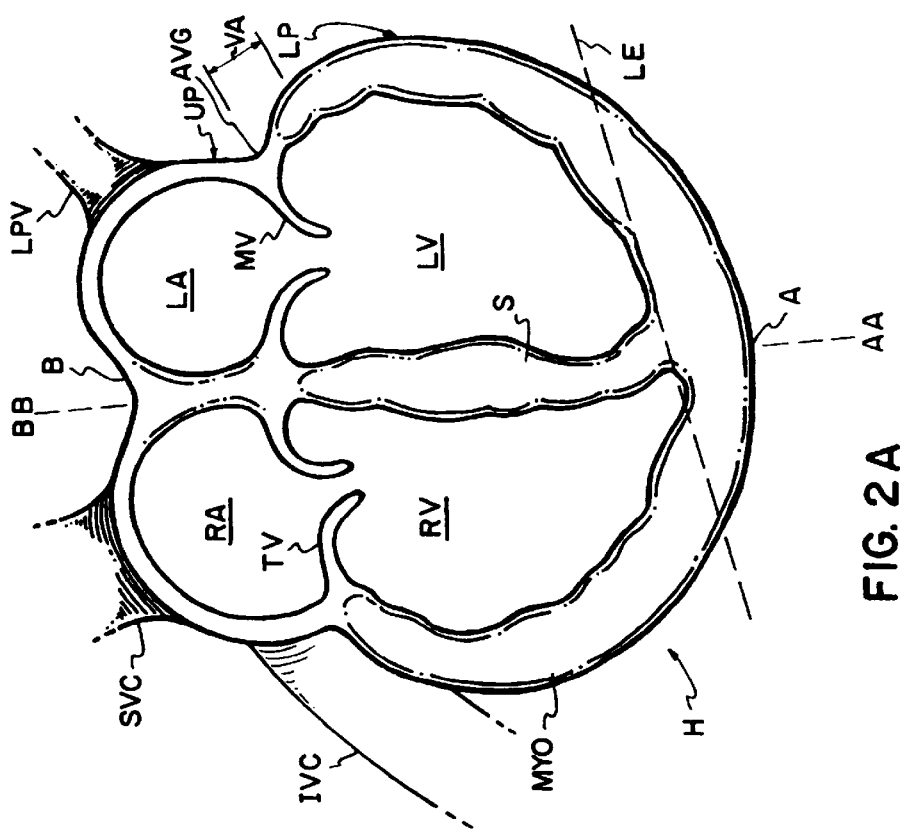
FIG. 2A is the view of FIG. 2 showing the heart during diastole.
Figure 2:
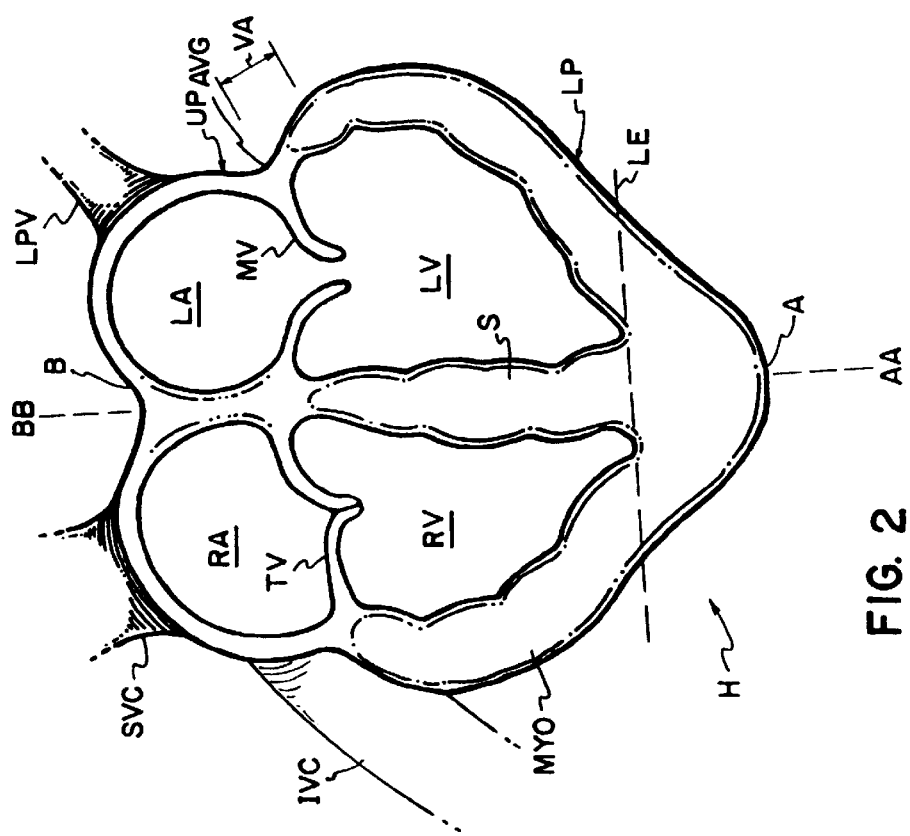
FIG. 2 is a schematic cross-sectional view of a diseased human heart shown during systole.

Comparing, FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H dilates outwardly between the apex A and the A-V groove AVG. So deformed, the diseased heart H during systole (FIG. 2) resembles the healthy heart H' during diastole (FIG. 1A). During diastole (FIG. 2A), the deformation is even more extreme.

As a diseased heart H enlarges from the representation of FIGS. 1 and 1A to that of FIGS. 2 and 2A, the heart H becomes a progressively inefficient pump. Therefore, the heart H requires more energy to pump the same amount of blood. Continued progression of the disease results in the heart H being unable to supply adequate blood to the patient's body and the patient becomes symptomatic of cardiac insufficiency.

For ease of illustration, the progression of congestive heart disease has been illustrated and described with reference to a progressive dilation of the lower portion LP of the heart H. While such enlargement of the lower portion LP is most common and troublesome, enlargement of the upper portion UP may also occur.

In addition to cardiac insufficiency, the enlargement of the heart H can lead to valvular disorders. As the circumference of the valvular annulus VA increases, the leaflets of the valves TV and MV may spread apart. After a certain amount of enlargement, the spreading may be so severe the leaflets cannot completely close. Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H.

B. Cardiac Constraint Therapy

Having described the characteristics and problems of congestive heart disease, a treatment method and apparatus are described in commonly assigned and copending U.S. patent application 09/114,757 filed Jul. 13, 1998. In general, a jacket is configured to surround the myocardium MYO. While the method of the present invention will be described with reference to a jacket as described in commonly assigned and copending U.S. patent application Ser. No. 09/114,757 filed Jul. 13, 1998, it will be appreciated the present invention is applicable to any cardiac constraint device including those shown in U.S. Pat. No. 5,800,528 and PCT International Publication No. WO 98/29401.

With reference now to FIGS. 3, 3A, 4 and 4A, the cardiac constraint device is shown as a jacket 10, 10' of flexible, biologically compatible material. For ease of illustration, the tensioning member of the present invention is not shown in FIGS. 3, 3A, 4 and 4A and will be separately described with reference to FIGS. 6 and 7.

The jacket 10, 10' is an enclosed knit material having upper and lower ends 12, 12', 14, 14'. The jacket 10, 10' defines an internal volume 16, 16' which is completely enclosed but for the open ends 12, 12' and 14'. In the embodiment of FIG. 3, lower end 14 is closed. In the embodiment of FIG. 4, lower end 14' is open. In both embodiments, upper ends 12, 12' are open. Throughout this description, the embodiment of FIG. 3 will be discussed. Elements in common between the embodiments of FIGS. 3 and 4 are numbered identically with the addition of an apostrophe to distinguish the second embodiment and such elements need not be separately discussed.

The jacket 10 is dimensioned with respect to a heart H to be treated. Specifically, the jacket 10 is sized for the heart H to be constrained within the volume 16. The jacket 10 can be slipped around the heart H. The jacket 10 has a length L between the upper and lower ends 12, 14 sufficient for the jacket 10 to constrain the lower portion LP. The upper end 12 of the jacket 10 extends at least to A-V groove AVG and further extends to the lower portion LP to constrain at least the lower ventricular extremities LE.

When the parietal pericardium is opened, the lower portion LP is free of obstructions for applying the jacket 10 over the apex A. If, however, the parietal pericardium is intact, the diaphragmatic attachment to the parietal pericardium inhibits application of the jacket over the apex A of the heart. In this situation, the jacket can be opened along a line extending from the upper end 12' to the lower end 14' of jacket 10'. The jacket can then be applied around the pericardial surface of the heart and the opposing edges of the opened line secured together after placed on the heart. Systems for securing the opposing edges are disclosed in, for example, U.S. Pat. No. 5,702,343, the entire disclosure of which is incorporated herein by reference. The lower end 14' can then be secured to the diaphragm or associated tissues using, for example, sutures, staples, etc.

Figure 3A:
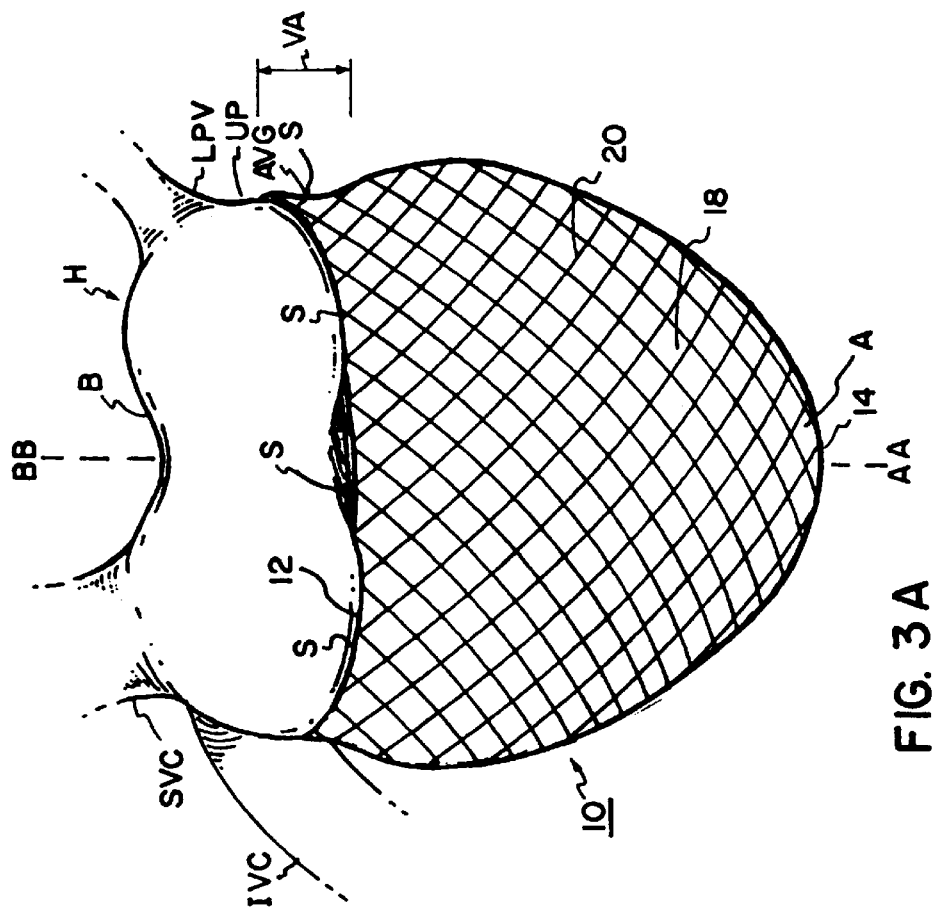
FIG. 3A is a side elevation view of a diseased heart in diastole with the device of FIG. 3 in place.
Figure 3:
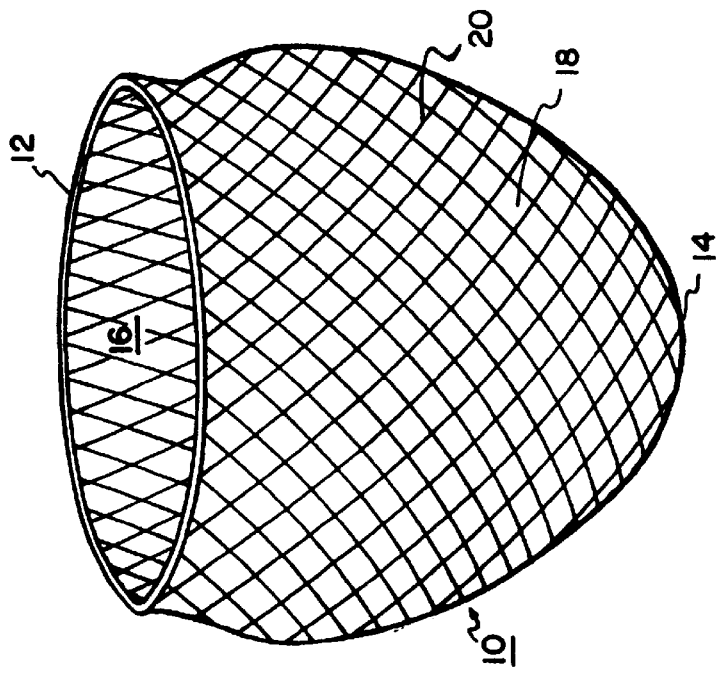
FIG. 3 is a perspective view of one embodiment of a cardiac constraint device.
Figure 4A:
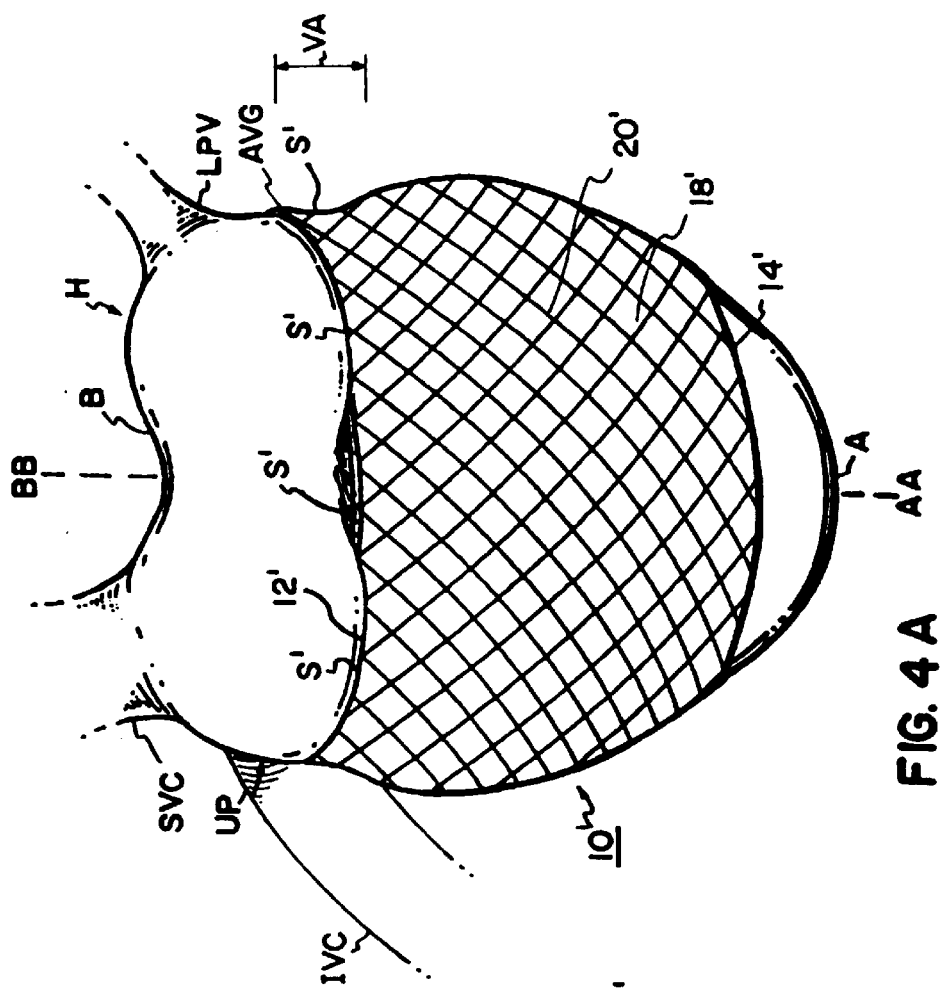
FIG. 4A is a side elevation view of a diseased heart in diastole with the device of FIG. 4 in place.
Figure 4:
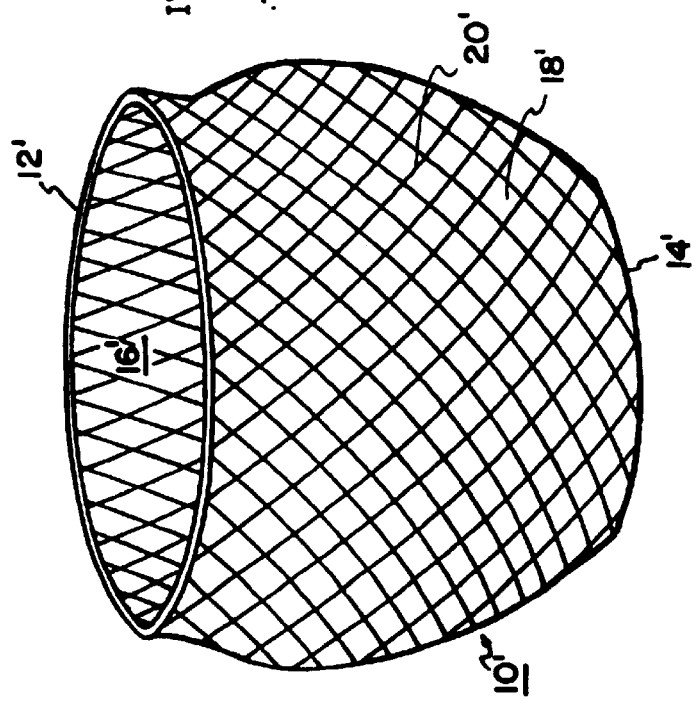
FIG. 4 is a perspective view of an alternative cardiac constraint device.

In the embodiment of FIGS. 3 and 3A, the lower end 14 is closed and the length L is sized for the apex A of the heart H to be received within the lower end 14 when the upper end 12 is placed at the A-V groove AVG. In the embodiment of FIGS. 4 and 4A, the lower end 14' is open and the length L' is sized for the apex A of the heart H to protrude beyond the lower end 14' when the upper end 12' is placed at the A-V groove AVG. The length L' is sized so that the lower end 14' extends beyond the lower ventricular extremities LE such that in both of jackets 10, 10', the myocardium MYO surrounding the ventricles RV, LV is in direct opposition to material of the jacket 10, 10' during diastole. Such placement is desirable for the jacket 10, 10' to present a constraint against dilation of the ventricular portions of the heart H.

After the jacket 10 is positioned on the heart H as described above, the jacket 10 is secured to the heart. Preferably, the jacket 10 is secured to the heart H using sutures (or other fastening means such as staples). The jacket 10 is sutured to the heart H at suture locations S circumferentially spaced along the upper end 12. While a surgeon may elect to add additional suture locations to prevent shifting of the jacket 10 after placement, the number of such locations S is preferably limited so that the jacket 10 does not restrict contraction of the heart H during systole.

While the jacket 10 is expandable due to its knit pattern, the fibers 20 of the knit fabric 18 are preferably non-expandable. While all materials expand to at least a small amount, the individual fibers 20 do not substantially stretch in response to force. In response to the low pressures in the heart H during diastole, the fibers 20 are generally inelastic. In a preferred embodiment, the fibers are 70 Denier polyester. While polyester is presently preferred, other suitable materials include polytetrafluoroethylene (PTFE), expanded PTFE (ePTFE) and polypropylene.

The knit material has numerous advantages. Such a material is flexible to permit unrestricted movement of the heart H (other than the desired constraint on circumferential expansion). The material is open defining a plurality of interstitial spaces for fluid permeability as well as minimizing the amount of surface area of direct contact between the heart H and the material of the jacket 10 (thereby minimizing areas of irritation or abrasion) to minimize fibrosis and scar tissue.

The open areas of the knit construction also allows for electrical connection between the heart and surrounding tissue for passage of electrical current to and from the heart. For example, although the knit material is an electrical insulator, the open knit construction is sufficiently electrically permeable to permit the use of trans-chest defibrillation of the heart. Also, the open, flexible construction permits passage of electrical elements (e.g., pacer leads) through the jacket. Additionally, the open construction permits visibility of the epicardial surface, thereby minimizing, limitations to performing other procedures, e.g., coronary bypass, to be performed without removal of the jacket.

The fabric 18 is preferably tear and run resistant. In the event of a material defect or inadvertent tear, such a defect or tear is restricted from propagation by reason of the knit construction.

The jacket 10 constrains further undesirable circumferential enlargement of the heart while not impeding other motion of the heart H. With the benefits of the present teachings, numerous modifications are possible. For example, the jacket 10 need not be directly applied to the epicardium (i.e., outer surface of the myocardium) but could be placed over the parietal pericardium. Further, an antifibrosis lining, (such as a PTFE coating on the fibers of the knit) could be placed between the heart H and the jacket 10. Alternatively, the fibers 20 can be coated with PTFE.

The jacket 10 can be used in early stages of congestive heart disease. For patients facing heart enlargement due to viral infection, the jacket 10 permits constraint of the heart H for a sufficient time to permit the viral infection to pass. In addition to preventing further heart enlargement, the jacket 10 treats valvular disorders by constraining circumferential enlargement of the valvular annulus and deformation of the ventricular walls.

C. Tensioning of the Jacket

Figure 5:
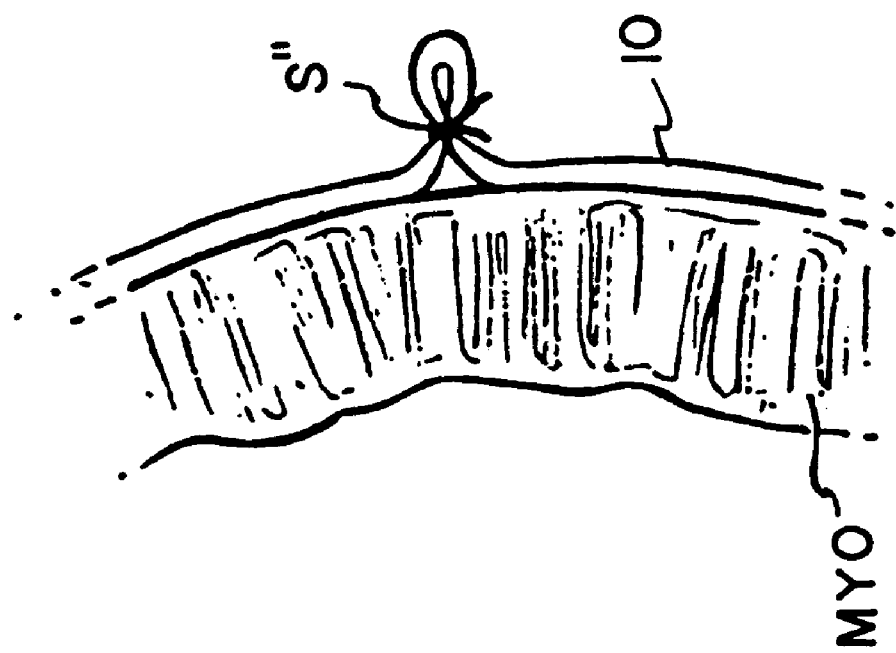
FIG. 5 is a cross-sectional view of the device of FIG. 3 overlying a myocardium and with the material of the device gathered for a snug fit.

To permit the jacket 10 to be easily placed on the heart H, the volume and shape of the jacket 10 are larger than the lower portion LP during diastole. So sized, the jacket 10 may be easily slipped around the heart H. Once placed, the jacket's volume and shape are adjusted for the jacket 10 to snugly conform to the external geometry of the heart H during diastole. Such sizing is easily accomplished due to the knit construction of the jacket 10. For example, excess material of the jacket 10 can be gathered and sutured S" (FIG. 5) to reduce the volume 16 of the jacket 10 and conform the jacket 10 to the shape of the heart H during diastole. Such shape represents a maximum adjusted volume. The jacket 10 constrains enlargement of the heart H beyond the maximum adjusted volume while preventing restricted contraction of the heart H during systole. As an alternative to gathering of FIG. 5, the jacket 10 can be provided with other arrangements for adjusting volume. For example, as disclosed in U.S. Pat. No. 5,702,343, the jacket can be provided with a slot. The edges of the slot can be drawn together to reduce the volume of the jacket.

The jacket 10 is adjusted to a snug fit on the heart H during diastole. Care is taken to avoid tightening the jacket 10 too much such that cardiac function is impaired. During diastole, the left ventricle LV fills with blood. If the jacket 10 is too tight, the left ventricle LV cannot adequately expand and left ventricular pressure will rise. During the fitting of the jacket 10, the surgeon can monitor left ventricular pressure. For example, a well-known technique for monitoring so-called pulmonary wedge pressure uses a catheter placed in the pulmonary artery. The wedge pressure provides an indication of filling pressure in the left atrium LA and left ventricle LV. While minor increases in pressure (e.g., 2–3 mm Hg) can be tolerated, the jacket 10 is snugly fit on the heart H but not so tight as to cause a significant increase in left ventricular pressure during diastole.

Figure 6:
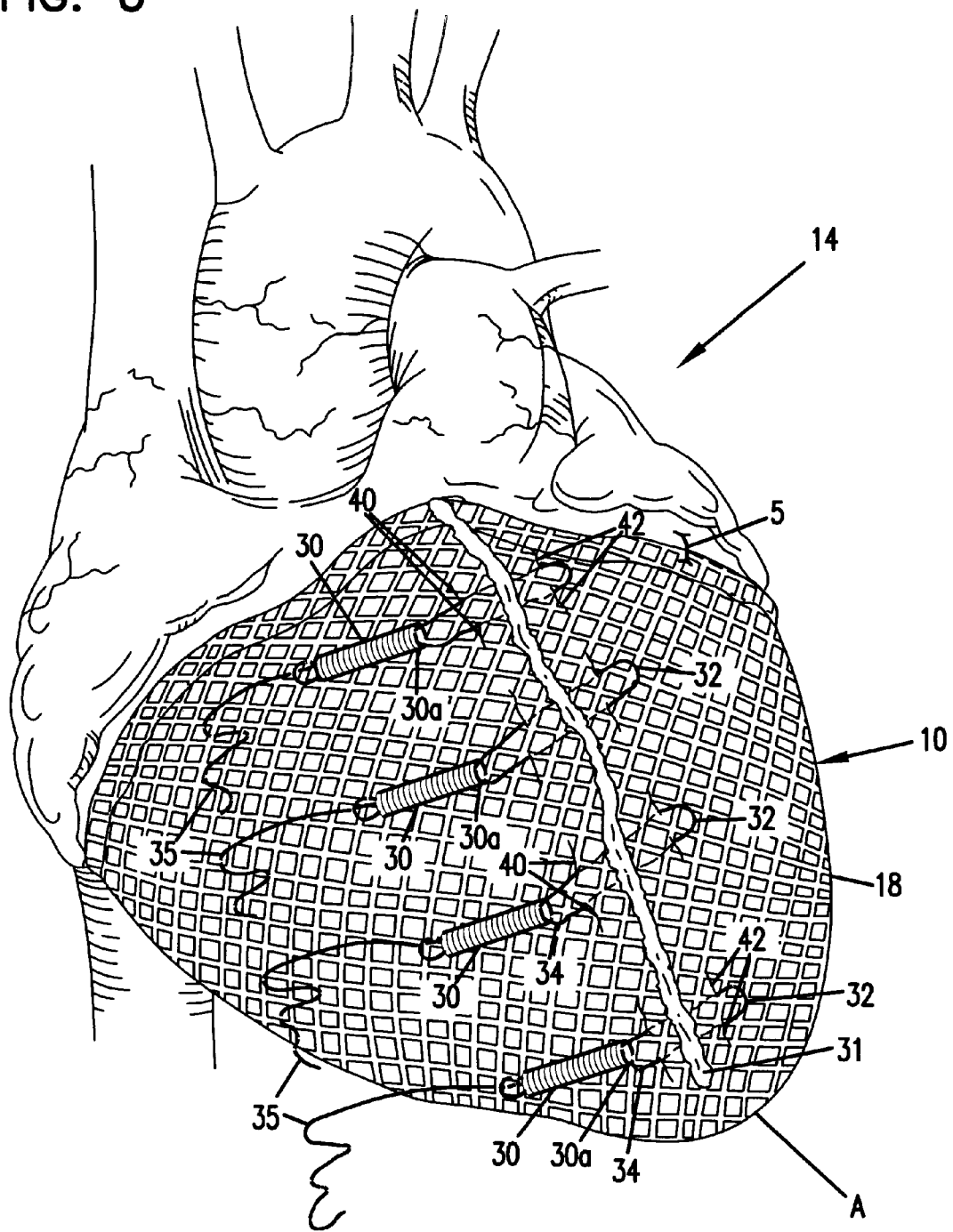
FIG. 6 is a view similar to FIG. 3A with the device including a releasable tensioning member and before application of tension on the tensioning member.

To facilitate a surgeon's ease of use, the present invention provides a releasable tensioning mechanism. In the embodiment shown, the tensioning member includes a spring 30 and associated length of suture 32 to act as a drawstring. The spring 30 may be stainless steel or other biocompatible material. The suture 32 may be commercially available suture material such as polyester or polypropylene. In FIG. 6, a seam 31 is shown formed in the material of the jacket 10 as part of the process of shaping flat sheet material into the shape of the jacket 10. The seam 31 extends generally parallel to the longitudinal axis of the jacket 10.

In FIG. 6, four tensioning members are shown spaced along the length of the jacket 10. While four members are shown, the number may vary. The draw string sutures 32 are passed through cells 40, 42 defined by the knit of the jacket fabric 18 on opposite sides of the seam 31. The springs 30 have first ends 30a secured to first ends 34 of the sutures 32 adjacent cells 40.

The draw string sutures 32 are entrained in the fabric 18 to pass beneath the seam 31 and be looped through cells 42 and passed back beneath the seam 31 and through cells 40 and into the cylindrical interior of springs 30. The drawstrings 32 are then passed between opposing coils of the spring 30 to a surgeon accessible free end 35.

The springs 30 are selected for the bias of the spring 30 to urge opposing coils of the spring 30 into abutting contact throughout the helix of the spring coil. Therefore, the free ends 35 of the draw strings 32 are captured by the spring 30 resisting movement of the draw strings 32 by any force insufficient to overcome the bias of the spring 30.

Figure 7:
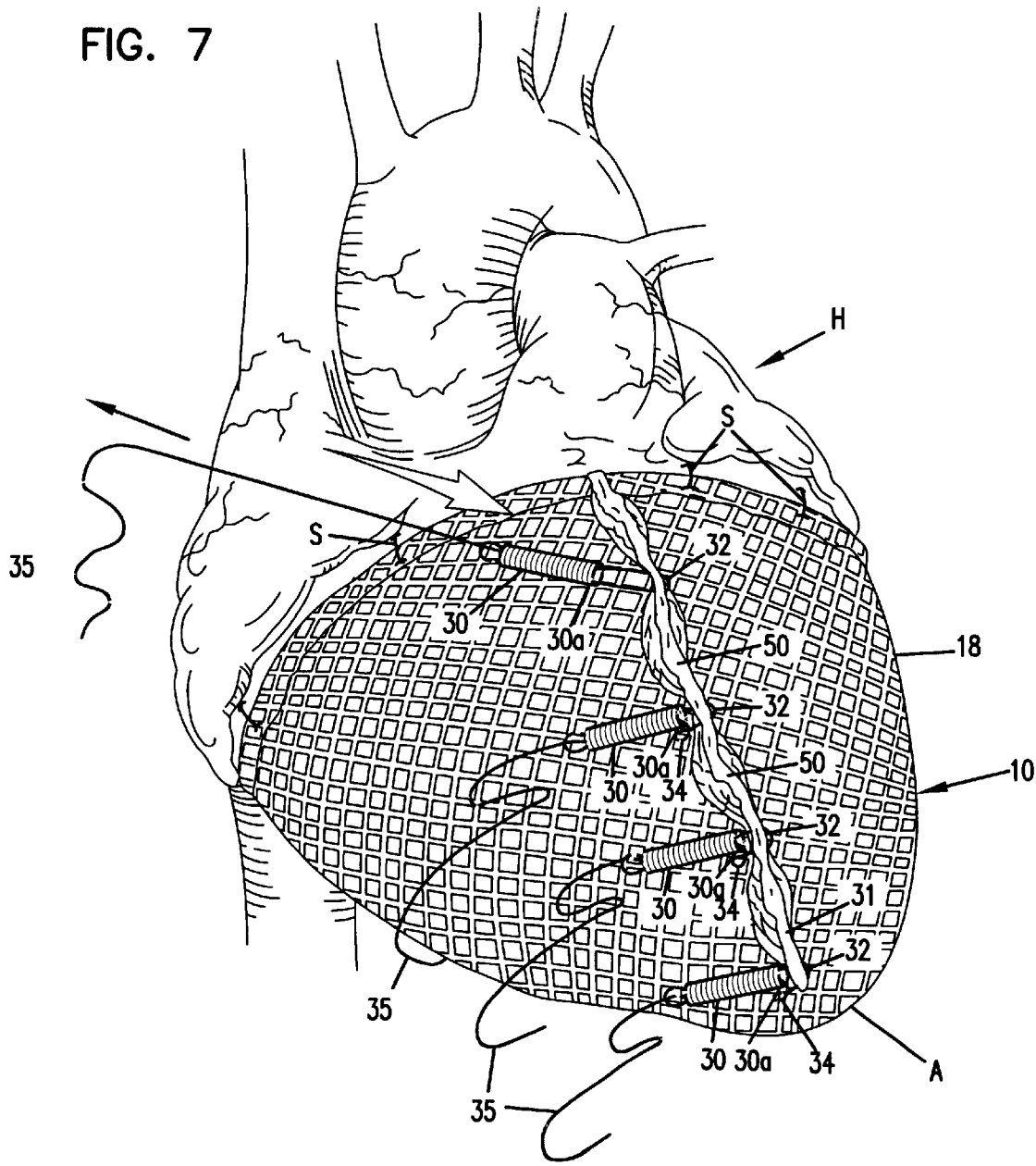
FIG. 7 is the view of FIG. 6 following application of tension on the tensioning member.

With the construction described above, a surgeon can tension the jacket 10 on the heart H by selectively pulling on the free ends 35 of the drawstrings 32. Such pulling overcomes the bias of the spring 30. Since the drawstring 32 is entrained through cells 40, 42, the cells 40, 42 are urged together during such pulling causing the fabric 18 to gather in bunches 50 as illustrated in FIG. 7. With the cells 40, 42 equally spaced from seam 31, the gathering occurs equally on both sides of the seam 31. Once all drawstrings 32 have been pulled, the bunches 50 can be sutured (as illustrated with suture S" in FIG. 5) to secure the degree of tensioning of the jacket 10. After such suturing, excess material of the bunches 50 can be removed by scalpel or the like. Further, at this time, the drawstrings 32 can be severed releasing the springs 30 to permit their easy removal.

The present invention offers numerous advantages. Having a plurality of tensioning members spaced along the longitudinal axis permits easy selective tensioning along the axis to accommodate variability in heart geometry. The springs 30 permit temporary holding of a degree of tensioning. For example, a surgeon can pull on free ends 35 to tension the jacket 10 and release the free ends 35 with the springs 30 holding the drawstrings 32 in place thereby holding the degree of tensioning. The surgeon is now free to perform any other procedure he or she may desire without losing the degree of tensioning. Further, the surgeon is free to monitor any equipment which might assist in measuring tension (e.g., equipment monitoring wedge pressure). If more tensioning is desired, the surgeon simply pulls more on the free ends 35. If less tensioning is desired, the surgeon can simply bend or stretch the springs 30 against the bias of the springs 30 to cause the opposing coils of the springs 30 to separate slightly a release the drawstrings 32 to release or reduce the degree of tensioning.

From the foregoing detailed description, the invention has been described in a preferred embodiment. Modifications and equivalents of the disclosed concepts are intended to be included within the scope of the appended claims.

What is claimed is:

1. A device for treating cardiac disease of a heart having a longitudinal axis from an apex to a base and having an upper portion and a lower portion divided by an A-V groove, said heart including a valvular annulus adjacent said A-V groove and ventricular lower extremities adjacent said apex, the device comprising:

a jacket of flexible material of knit construction defining a volume between an open upper end and a lower end, said jacket dimensioned for said apex of said heart to be inserted into said volume through said open upper end and for said jacket to be slipped over said heart, said jacket further dimensioned for said jacket to have a longitudinal dimension between said upper and lower ends sufficient for said jacket to constrain said lower portion with said jacket constraining said valvular annulus and further constraining said ventricular lower extremities;

said jacket adapted to be secured to said heart with said jacket having portions disposed on opposite sides of the heart between said valvular annulus and said ventricular lower extremities; and said jacket adapted to be adjusted on said heart to snugly conform to an external geometry of said heart and assume a maximum adjusted volume for said jacket to constrain circumferential expansion of said heart beyond said maximum adjusted volume during diastole and permit substantially unimpeded contraction of said heart during systole;

a flexible draw string laced through said material with one end of the draw string fixed in place and with the other end displaceable relative to the material in response to a tension on the draw string for the knit material to be bunched together in response to relative movement between the ends of the draw string;

a releasable stay member for holding said draw string in a fixed position relative to said jacket upon release of a pulling tension on said draw string with said stay member releasable in response to a resumed pulling tension on said draw string.

2. A device for treating cardiac disease of a heart according to claim 1 wherein said releasable stay member is a spring secured to said jacket, said draw string being passed through abutting coils of said string with said coils biased to abut with a force sufficient to immobilize said draw string when said pulling tension is released and permit said draw string to be pulled through said coils when said pulling tension is resumed.

* * * * *